United States Patent [19]

Torii et al.

[11] Patent Number: 4,464,237
[45] Date of Patent: Aug. 7, 1984

[54] PROCESS FOR PREPARING β-LACTAM DERIVATIVES

[75] Inventors: Sigeru Torii; Hideo Tanaka; Junzo Nokami; Takashi Shiroi; Michio Sasaoka, all of Okayama; Norio Saito, Tokushima, all of Japan

[73] Assignee: Otsuka Kagaku Yakuhin Kabushiki Kaisha, Japan

[21] Appl. No.: 406,519

[22] Filed: Aug. 9, 1982

[51] Int. Cl.³ .............................................. C25B 3/06
[52] U.S. Cl. ..................................... 204/81; 204/59 R
[58] Field of Search .................... 204/59 R, 72, 73 R, 204/81

[56] References Cited
PUBLICATIONS

Balsamo et al., Tetrahedron Letters, vol. 23, No. 29, pp. 2991–2994 7/82.

Primary Examiner—John F. Niebling
Attorney, Agent, or Firm—Larson and Taylor

[57] ABSTRACT

This invention provides a process for preparing a β-lactam derivative represented by the formula

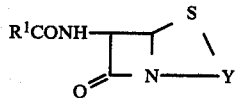

wherein $R^1$ represents aralkyl group or aryloxy methyl group, Y represents the group

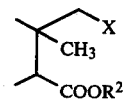

(wherein $R^2$ represents aryl-substituted lower alkyl group, aryloxy-substituted lower alkyl group or lower alkyl group optionally substituted with halogen atom and X represents halogen atom) or the group

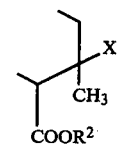

(wherein $R^2$ and X are as defined above), the process comprising electrolyzing an azetidinone derivative of the formula

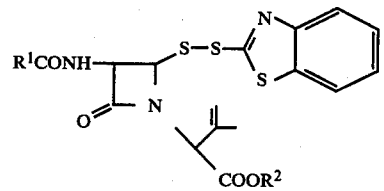

wherein $R^1$ and $R^2$ are as defined above in the presence of hydrohalogenic acid and/or halide.

8 Claims, No Drawings

PROCESS FOR PREPARING β-LACTAM DERIVATIVES

This invention relates to a novel process for preparing β-lactam derivatives and particularly to a novel process for preparing β-lactam derivatives represented by the formula

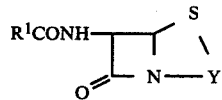

wherein $R^1$ represents aralkyl group or aryloxy methyl group, Y represents the group

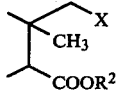

(wherein $R^2$ represents aryl-substituted lower alkyl group, aryloxy-substituted lower alkyl group or lower alkyl group optionally substituted with halogen atom and X represents halogen atom) or the group

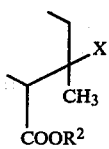

(wherein $R^2$ and X are as defined above).

The β-lactam derivatives of the formula (I) are known compounds and useful as the intermediates for synthesizing penicillin-type or cephalosporin-type antibiotics. For example, according to the process schematically illustrated below, the compounds of the present invention can be made into cephalosporin-type compounds of the formulae (IIa), (IIb) and (IIc), respectively useful as antibacterial agents.

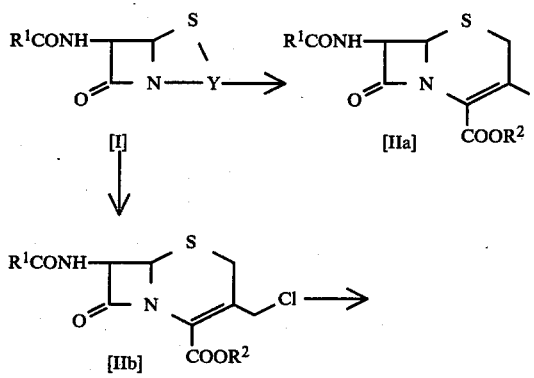

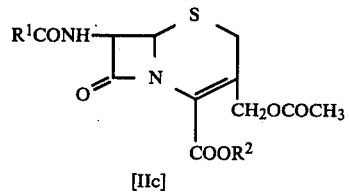

In the formulae shown above, $R^1$, $R^2$ and Y are as defined hereinbefore.

Heretofore the following processes have been known for preparing β-lactam derivatives of the formula (I): (1) a process in which penicillin sulfoxide is thermally decomposed to the corresponding sulfenic acid which is reacted with thionyl chloride and triethylamine or with phosphorus tribromide [Kukolja, J.A.C.S., 97, 3192–3198 (1975)]; (2) a process in which bromine or chlorine is made to act on an azetidinone derivative represented by the formula

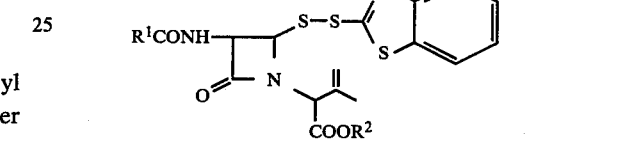

wherein $R^1$ and $R^2$ are as defined above [T. Kamiya, Tetrahedron Letters, 3001 (1973)], (3) a process in which cupric chloride or mercuric chloride is reacted with the azetidinone derivative of the formula (III) [Yuki Gosei Kagaku (Organic Synthesis), 33, 24 (1975)], etc. However, these processes are commercially unfavorable because they suffer at least one of the following disadvantages: requiring special halogenating agents; employing severe reaction conditions; entailing a complicated procedure; being unable to give end products in high yields; producing by-products involving difficult waste disposal; etc.

It is an object of this invention to provide a process for preparing β-lactam derivatives of the formula (I) in a commercially favored manner.

It is another object of the invention to provide a process for preparing in high yields the β-lactam derivatives under mild reaction conditions by simplified procedure without use of a special reagent.

It is a further object of the invention to provide a process for preparing the β-lactam derivatives which facilitates the separation and purification of the β-lactam derivatives and which is free from the problems in respect of disposal of by-products or like waste.

Other features and advantages of the present invention will become apparent from the following description.

According to this invention, a β-lactam derivative of the formula (I) is prepared by electrolyzing the azetidinone derivative of the formula (III).

Examples of the aralkyl groups represented by $R^1$ in the present invention are benzyl, p-nitrophenylmethyl, p-hydroxyphenylmethyl, p-chlorophenylmethyl, diphenylmethyl, 2-phenylethyl, etc; examples of the aryloxymethyl groups are phenoxymethyl, p-nitrophenyloxymethyl, p-hydroxyphenyloxymethyl, etc. Examples of the aryl-substituted lower alkyl groups represented by $R^2$ are benzyl, p-nitrobenzyl, diphenylmethyl, 2- phenylethyl, 2-(p-nitrophenyl)ethyl, 3-phenylpropyl, 3-(p-nitrophenyl)propyl, etc.; the aryloxy-substituted lower alkyl groups include phenoxymethyl, p-nitrophenoxymethyl, 2-phenoxyethyl, 2-(p-nitrophenoxy)ethyl, 3-phenoxypropyl, 3-(p-nitrophenoxy)propyl, etc.; the lower alkyl groups optionally substituted with halogen atoms are methyl, ethyl, n-propyl, isopropyl, n-butyl, tert-butyl, 2-chloroethyl, 2,2,2-trichloroethyl, etc. Examples of the halogen atoms represented by X are chlorine, bromine, iodine, etc.

The azetidinone derivatives of the formula (III) serving as the starting material in the present invention are known compounds and easily prepared, for example, from penicillin sulfoxide derivatives [Kamiya, Tetrahedron Letters, 3001 (1973)].

The azetidinone derivative of the formula (III) is electrolyzed in the presence of a hydrohalogenic acid and/or halide by passing an electric current through the electrolyte. Useful hydrohalogenic acids include those heretofore known such as hydrochloric acid, hydrobromic acid, hydroiodic acid, etc. Examples of halides useful in this invention are a wide variety of known ones including sodium chloride, potassium chloride, lithium chloride, magnesium chloride, barium chloride, calcium chloride, aluminum chloride and like chlorides, sodium bromide, potassium bromide, lithium bromide, magnesium bromide, calcium bromide, barium bromide and like bromides, sodium iodide, potassium iodide, lithium iodide, magnesium iodide, calcium iodide, barium iodide and like iodides, etc. The amounts of the hydrohalogenic acid and/or halide to be used are not particularly limited and can be suitably determined over a wide range. They are used in an amount of usually about 0.1 to about 20 moles, preferably about 0.5 to about 10 moles, per mole of the compound of the formula (III). The reaction of the present invention is enhanced when a mineral acid or organic acid is added to the reaction system. Useful mineral acids include sulfuric acid, nitric acid, carbonic acid, sodium hydrogensulfate, potassium hydrogensulfate, phosphoric acid, boric acid, etc. Examples of useful organic acids are formic acid, acetic acid, propionic acid, oxalic acid, citric acid, phthalic acid, p-toluenesulfonic acid, methanesulfonic acid, etc. The mineral acid or organic acid is used in an amount of usually about 0.1 to about 10 moles, preferably about 0.5 to about 10 moles, per mole of the compound of the formula (III). Generally used as a solvent in the electrolysis is a mixture of water and a suitable organic solvent. Useful organic solvents are for example acetonitrile, butyronitrile, propionitrile and like nitriles, dichloromethane, dichloroethane, chloroform, carbon tetrachloride, dibromoethane and like hydrocarbon halides, diethylether, dibutylether, dioxane, tetrahydrofuran and like ethers, methyl acetate, ethyl acetate, ethyl formate, methyl propionate and like esters or mixtures thereof.

The electrolysis of the compound (III) is carried out at either controlled potential or constant current. The current density is in the range of usually about 1 to about 500 mA/cm² and preferably about 5 to about 200 mA/cm². The required electric charge is usually about 2 to about 20 F/mol preferably about 3 to about 10 F/mol, although variable depending on the concentration of the substrate, the kind of solvent, the type or shape of electrolytic bath. Useful electrodes include those usually used, such as those of platinum, carbon, stainless steel, titanium, nickel or the like. The reaction temperature is not particularly limited as far as it is below a level at which there occurs the decomposition or conversion of the starting material and reaction product. It is usually about −30° to about 100° C., preferably about −10° to about 70° C. The electrolytic bath is used with or without a diaphragm.

When electrolyzing the compound (III) in the presence of hydrochloric acid and/or chloride as the hydrohalogenic acid and/or halide, β-lactam derivative of the formula (Ia)

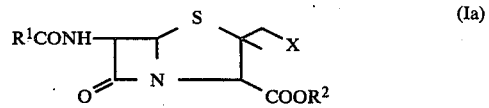

wherein $R^1$, $R^2$ and X are as defined above is selectively formed. When using hydroiodic acid and/or iodide in the electrolysis, β-lactam derivative of the formula (Ib)

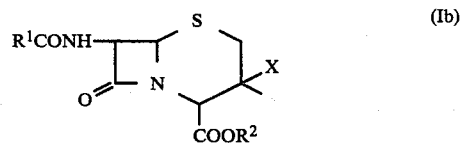

wherein $R^1$, $R^2$ and X are as defined above is selectively produced. The use of hydrobromic acid and/or bromide in the electrolysis gives a mixture of compound of the formula (Ia) and compound of the formula (Ib).

The compounds of this invention thus produced are easily isolated from the reaction mixture and purified by a usual method of separation such as solvent extraction, column chromatography, etc.

According to the process of this invention, the compound as contemplated are prepared in high yields under mild conditions by simplified procedure without using any special reagent. Further the present process facilitates the separation and purification of end products and is free from the problems arising from the disposal of by-products and like waste. For these reasons, the present process is extremely advantageous from commercial points of view.

The present invention will be described below in detail with reference to examples.

EXAMPLE 1

85.4 mg of a compound of the formula (III) (wherein $R^1$ is benzyl and $R^2$ is methyl) and 745.6 mg of anhydrous magnesium chloride were mixed with 3 ml of water and 5 ml of methylene chloride and stirred. Electrolysis was continued with use of platinum electrodes (3 cm²) at a temperature of 26° to 28° C. by passing an electric current of 30 mA for 53 minutes (which corresponded to an electric charge of 6 F/mol) through the electrolyte. The reaction mixture was separated into a methylene chloride layer and an aqueous layer. The aqueous layer was extracted with methylene chloride. The methylene chloride layer was added to the extract. Then the mixture was washed with water and dried over anhydrous sodium sulfate. The solvent was removed at reduced pressure and the residue was separated and purified by silica gel column chromatography using a 5:1 benzene-ethyl acetate mixture as a developer, giving 59.0 mg of a compound of the formula (Ia)

(wherein R¹ is benzyl, R² is methyl and X is chlorine) in a yield of 93%.

IR(CHCl$_3$, cm$^{-1}$) 3420, 1785, 1748, 1673

NMR(CDCl$_3$, δ, ppm) 1.50(s, 3H), 3.42(s, 2H), 3.61(s, 2H), 3.74(s, 3H), 4.87(s, 1H), 5.52, 5.59(d, q, 2H), 6.40(d, 1H), 7.30(s, 5H)

EXAMPLES 2 TO 8

The same procedure as in Example 1 was repeated under the conditions shown in Table 1 below, producing compounds (I) in the yields indicated in Table 1. The compounds produced were identified by IR and NMR spectroscopic analyses.

TABLE 1

| Ex. | Starting Comp. (III) R¹ = benzyl R² = methyl | Hydrohalogenic acid or halide | | Solvent | Yeild of Comp. (I) R¹ = benzyl R² = methyl |
|---|---|---|---|---|---|
| 2 | 80.2 (mg) | NaCl | 4.27 (m mol/ml water) | CH$_2$Cl$_2$/H$_2$O (ml/ml) 5/2 | 85 (%) |
| 3 | 82.0 | NaCl | 5.15 | 5/3 | 96 |
| 4 | 79.6 | NaCl | 5.13 | 2/5 | 63 |
| 5 | 83.8 | MgCl$_2$ | 2.01 | 6/2 | 86 |
| 6 | 79.7 | BaCl$_2$ | 1.31 | 5/3 | 69 |
| 7 | 74.4 | AlCl$_3$ | 0.80 | 5/3 | 67 |
| 8 | 82.8 | HCl | | 5/3 | 65 |

EXAMPLE 9

A 80.7 mg quantity of compound of the formula (III) (wherein R¹ is benzyl and R² is methyl) and 33.2 mg of anhydrous magnesium chloride were added to 0.3 ml of water and 6 ml of acetonitrile and stirred. Electrolysis was continued with use of platinum electrodes (3 cm$^2$) at a temperature of 27° to 29° C. by passing a current of 30 mA for 34 minutes (which corresponded to an electric charge of 4 F/mol through the electrolyte.) Thereafter, 3 ml of water was added to the reaction mixture, and the admixture was extracted with 30 ml of ethyl acetate. The extract was treated in the same manner as in Example 1, giving 55.48 mg of compound (Ia) (wherein R¹ is benzyl, R² is methyl and X is chlorine) in a yield of 92%.

The compound thus prepared was identified by IR and NMR spectroscopic analyses.

EXAMPLE 10

A 80.1 ml quantity of compound of the formula (III) (wherein R¹ is benzyl and R² is methyl) and AlCl$_3$.6H$_2$O (22.8 mg) were added to a mixture of 0.3 ml of water, 6 ml of acetonitrile and 1.5 ml of tetrahydrofuran and stirred. With use of platinum electrodes, the same procedure as in Example 9 was repeated giving 55.04 mg of compound of the formula (Ia) (wherein R¹ is benzyl, R² is methyl and X is chlorine) in a yield of 92.6%. The compound thus prepared was identified by IR and NMR spectroscopic analyses.

EXAMPLE 11

A 80.9 mg quantity of compound (III) (wherein R¹ is benzyl and R² is methyl) and 52.4 mg of MgBr$_2$.6H$_2$O were added to a mixture of 0.3 ml of water, 6 ml of acetonitrile and 1.5 ml of tetrahydrofuran and agitated. Electrolysis was continued with use of platinum electrode (3 cm$^2$) at a temperature of 5° to 9° C. by passing a current of 30 mA for 34 minutes (which corresponded to an electric charge of 4 F/mol) through the electrolyte. The same subsequent treatment as in Example 9 gave 53.7 mg (yield: 80%) of compound of the formula (Ia) (wherein R¹ is benzyl, R² is methyl and X is bromine) and 13.4 mg (yield: 20%) of compound of the formula (Ib) (wherein R¹, R² and X are as defined above). Total yield: quantitative.

[Ia] (R¹=benzyl, R²=methyl, X=bromine)
 IR(cm$^{-1}$)3290, 1779, 1743, 1655
 NMR(CDCl$_3$, δ, ppm) 1.53(s, 3H), 3.31(s, 2H), 3.60 (s, 2H), 3.74(s, 3H), 4.94(s, 1H), 5.53(q, 1H), 5.61(d, 1H), 6.70 (d, 1H), 7.30(s, 5H)

[Ib] (R¹=benzyl, R²=methyl, X=bromine)
 IR(cm$^{-1}$)3280, 1774, 1738, 1661
 NMR(CDCl$_3$, δ, ppm) 1.85(s, 3H), 2.73, 3.50(ABq, 2H), 3.63(s, 2H), 3.74(s, 3H), 4.79(s, 1H), 5.27(d, 1H), 5.59(q, 1H), 6.72(d, 1H), 7.32(s, 5H)

EXAMPLES 12 TO 24

The procedure of Example 11 was repeated except that it was carried out under the conditions as shown in Table 2 below using compounds (III), giving compounds of the formula (Ia) and (Ib) in the yields tabulated in Table 2.

TABLE 2

| Example | Starting comp. [III] (mg) | Solvent (ratio in ml) | Hydrohalogenic acid or halide | (mg) | Temperature (°C.) | Yield of comp. (%) [Ia], [Ib] |
|---|---|---|---|---|---|---|
| 12 | 83.3 | H$_2$O/MeCN/THF 0.3/6.0/1.5 | NaBr | 18.7 | 21~23 | 5, 87 |
| 13 | 79.8 | H$_2$O/MeCN/THF 0.3/6.0/1.5 | NaBr | 18.7 | −3~−5 | 48, 48 |
| 14 | 80.2 | H$_2$O/MeCN/THF 0.3/1.0/7.5 | NaBr | 18.4 | 20~23 | 33, 61 |
| 15 | 80.0 | H$_2$O/THF 1.0/7.0 | NaBr | 20.0 | 23~26 | 46, 39 |
| 16 | 80.7 | H$_2$O/DME 0.3/7.0 | NaBr | 19.7 | 29~50 | 4, 71 |
| 17 | 81.0 | H$_2$O/DMF 0.3/7.5 | NaBr | 18.5 | 24~26 | 4, 86 |
| 18 | 81.4 | H$_2$O/MeCN/THF 0.3/6.0/1.5 | KBr | 24.7 | 26~30 | 46, 46 |
| 19 | 80.0 | H$_2$O/MeCN/THF 0.3/6.0/1.5 | LiBr.H$_2$O | 20.0 | 23~32 | 35, 57 |

TABLE 2-continued

| Example | Starting comp. [III] (mg) | Solvent (ratio in ml) | Hydrohalogenic acid or halide (mg) | | Temperature (°C.) | Yield of comp. (%) [Ia], [Ib] |
| --- | --- | --- | --- | --- | --- | --- |
| 20 | 85.8 | H$_2$O/MeCN/THF 0.3/6.0/1.5 | MgBr$_2$.6H$_2$O | 57.5 | 23~27 | 53, 45 |
| 21 | 84.0 | H$_2$O/MeCN/THF 0.3/6.0/1.5 | MgBr$_2$.6H$_2$O | 57.0 | −3~−5 | 85, 11 |
| 22 | 82.0 | H$_2$O/MeCN/Et$_2$O 0.3/6.0/1.5 | MgBr$_2$.6H$_2$O | 56.8 | −3~−5 | 48, 48 |
| 23 | 81.0 | H$_2$O/MeCN/DME 0.3/6.0/1.5 | MgBr$_2$.6H$_2$O | 54.1 | −3~−6 | 40, 50 |
| 24 | 81.0 | H$_2$O/MeCN/THF 0.3/6.0/1.5 | 47% HBr | 30.7 | 23~24 | 56, 30 |

EXAMPLE 25

A 80.7 mg quantity of compound of the formula (III) (wherein $R^1$ is benzyl and $R^2$ is methyl) and 25.0 mg of sodium iodide were added to a mixture of 0.3 ml of water, 6 ml of acetonitrile and 1.5 ml of tetrahydrofuran and stirred. The same subsequent treatment as in Example 11 was conducted by using platinum electrodes, followed by the same procedure as therein. There was produced 56.2 mg of a compound of the formula (Ib) (wherein $R^1$ is benzyl, $R^2$ is methyl and X is iodine) in a yield of 76%.

NMR(CDCl$_3$ δ, ppm) 2.12(s, 3H), 2.66, 3.02(ABq, 2H), 3.68(d, 2H), 3.75(s, 3H), 4.80(s, 1H), 5.26(d, 1H), 5.59(q, 1H), 6.61(d, 1H), 7.38(s, 5H)

EXAMPLE 26

83.0 mg of compoud of the formula (III) (wherein $R^1$ is phenoxymethyl and $R^2$ is methyl) and 25.1 mg of sodium iodide were added to 0.6 mg of water and 1.5 mg of tetrahydrofuran, and stirred. The resultant mixture was subjected to the same electrolysis as in Example 11 to obtain the desired product of the formula (Ib) (wherein R is phenoxymethyl, R is methyl and X is iodide) in a yield of 73%.

NMR(CDCl$_3$, δ, ppm) 2.12(s, 3H), 2.72, 3.06(ABq, 2H), 3.78(s, 3H), 4.59(s, 2H), 4.87 (s, 1H), 5.30(d, 1H), 5.70(dd, 1H), 6.85–7.80(m, 6H)

EXAMPLES 27 TO 29

The similar procedure as in Example 20 was followed using compounds of the formula (III) shown in Table 3 below. Results are also given in Table 3.

TABLE 3

| Example | Starting material [III] | Yield | NMR (CDCl$_3$, δ, ppm) |
| --- | --- | --- | --- |
| 27 | $R^1$ = phenoxymethyl $R^2$ = methyl 87.8 mg | [Ia] 40% | 1.60 (s,3H) 3.45 (s,2H) 3.80 (s,3H) 4.60 (s,2H) 5.01 (s,1H) 5.52–5.83 (m,2H) 7.00–8.50 (m,6H) |
| | | [Ib] 53% | 1.90 (s,3H) 2.76, 3.60 (ABq,2H) 3.77 (s,3H) 4.57 (s,2H) 4.87 (s,1H) 5.31 (d,1H) 6.8–7.7 (m,6H) |
| 28 | $R^1$ = benzyl $R^2$ = 2,2,2-trichloroethyl 99.6 mg | [Ia] 50% | 1.64 (s,3H) 3.30 (s,2H) 3.66 (s,2H) 4.78 (s,2H) 5.09 (s,1H) 5.46–5.73 (m,2H) 6.28 (d,1H) 7.33 (s,5H) |
| | | [Ib] 47% | 1.97 (s,3H) 2.78, 3.52 (ABq,2H) 3.65 (s,2H) 4.80 (s,2H) 4.97 (s,1H) 5.28 (d,1H) 5.62 (dd,1H) 7.30 (s,6H) |
| 29 | $R^1$ = benzyl $R^2$ = benzyl 91.8 mg | [Ia] 38% | 1.45 (s,3H) 3.26 (s,2H) 3.60 (s,2H) 4.95 (s,1H) 5.16 (s,2H) 5.35–5.65 (m,2H) 6.50 (d,1H) 7.25 (s,5H) 7.28 (s,5H) |
| | | [Ib] 51% | 1.74 (s,3H) 2.70, 3.43 (ABq,2H) 3.58 (s,2H) 4.68 (s,1H) 5.11 (s,2H) 5.20 (d,1H) 5.55 (dd,1H) 6.67 (d,1H) 7.27 (s,5H) 7.30 (s,5H) |

We claim:

1. A process for preparing a β-lactam derivative represented by the formula

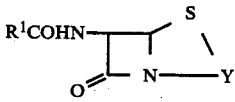

wherein $R^1$ represents aralkyl group or aryloxy methyl group, Y represents the group

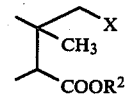

(wherein $R^2$ represents aryl-substituted lower alkyl group, aryloxy-substituted lower alkyl group or lower alkyl group optionally substituted with halogen atom and X represents halogen atom) or the group

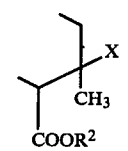

(wherein $R^2$ and X are as defined above), the process comprising electrolyzing an azetidinone derivative of the formula

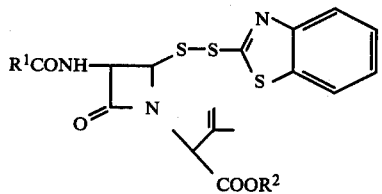

wherein $R^1$ and $R^2$ are as defined above in the presence of hydrohalogenic acid and/or metal halide, at a current density of about 5 to about 200 mA/cm$^2$ and at a temperature of about $-30°$ to about 100° C.

2. A process as defined in claim 1 in which the hydrohalogenic acid and/or halide is present in the reaction system in an amount of about 0.1 to about 20 moles per mole of the compound of the formula (III).

3. A process as defined in claim 1 or 2 in which the hydrohalogenic acid is hydrochloric acid, hydrobromic acid or hydroiodic acid.

4. A process as defined in claim 1 or 2 in which the halide is sodium chloride, potassium chloride, lithium chloride, magnesium chloride, barium chloride, calcium chloride, aluminum chloride, sodium bromide, potassium bromide, lithium bromide, magnesium bromide, calcium bromide, barium bromide, sodium iodide, potassium iodide, lithium iodide, magnesium iodide, calcium iodide or barium iodide.

5. A process as defined in any one of claims 1 to 4 in which the electrolysis is carried out in the presence of mineral acid or organic acid.

6. A process as defined in claim 5 in which the mineral acid or organic acid is present in the reaction system in an amount of about 0.1 to about 10 moles per mole of the compound of the formula (III).

7. A process as defined in claim 6 in which the mineral acid is sulfuric acid, nitric acid, carbonic acid, sodium hydrogensulfate, potassium hydrogensulfate, phosphoric acid or boric acid.

8. A process as defined in claim 6 in which the organic acid is formic acid, acetic acid, propionic acid, oxalic acid, citric acid, phthalic acid, p-toluenesulfonic acid or methanesulfonic acid.

* * * * *